(12) United States Patent
Newton et al.

(10) Patent No.: US 6,883,778 B1
(45) Date of Patent: Apr. 26, 2005

(54) APPARATUS FOR REDUCING FLUID DRAWBACK THROUGH A MEDICAL VALVE

(75) Inventors: Brian L. Newton, Woonsocket, RI (US); Charles F. Ganem, Cape Neddick, ME (US)

(73) Assignee: Nypro Inc., Clinton, MA (US)

( * ) Notice: Subject to any disclaimer, the term of this patent is extended or adjusted under 35 U.S.C. 154(b) by 0 days.

(21) Appl. No.: 09/479,327

(22) Filed: Jan. 6, 2000

Related U.S. Application Data

(63) Continuation-in-part of application No. 09/394,169, filed on Sep. 13, 1999, now Pat. No. 6,039,302, which is a continuation of application No. 08/970,125, filed on Nov. 13, 1997, now abandoned.

(60) Provisional application No. 60/117,359, filed on Jan. 27, 1999, provisional application No. 60/034,708, filed on Jan. 3, 1997, and provisional application No. 60/031,175, filed on Nov. 18, 1996.

(51) Int. Cl.⁷ .................................................. A61M 5/00
(52) U.S. Cl. .................... 251/149.1; 604/256; 604/905
(58) Field of Search .............................. 604/905, 249, 604/246; 251/149.1, 149.6

(56) References Cited

U.S. PATENT DOCUMENTS

| | | | |
|---|---|---|---|
| 2,594,405 A | 4/1952 | Deters | 137/53 |
| 2,693,801 A | 11/1954 | Foreman | 128/214 |
| 2,705,501 A | 4/1955 | Fritzsch | 137/113 |
| 2,756,740 A | 7/1956 | Deane | 128/1 |
| 2,899,975 A | 8/1959 | Fernandez | 137/543.17 |
| 2,999,499 A | 9/1961 | Willet | 128/214 |
| 3,087,492 A | 4/1963 | Garth | 128/350 |
| 3,105,511 A | 10/1963 | Murphy, Jr. | 137/399 |
| 3,192,949 A | 7/1965 | De See | 137/540 |
| 3,385,301 A | 5/1968 | Harautuneian | 128/349 |
| 3,399,677 A | 9/1968 | Gould et al. | 128/349 |
| 3,416,567 A | 12/1968 | Von Dardel et al. | 137/604 |
| 3,506,005 A | 4/1970 | Gilio et al. | 128/214 |
| 3,538,950 A | 11/1970 | Porteners | 137/608 |
| 3,570,484 A | 3/1971 | Steer | 128/214 |
| 3,572,375 A | 3/1971 | Rosenberg | 137/512 |
| 3,726,282 A | 4/1973 | Patel | 128/349 BV |
| 3,806,086 A | 4/1974 | Cloyd | 251/149.7 |
| 3,831,629 A | 8/1974 | Mackal et al. | 137/525 |
| 3,923,065 A | 12/1975 | Nozick et al. | 128/348 |
| 3,965,910 A | 6/1976 | Fischer | 128/349 |
| 3,994,293 A | 11/1976 | Farro | 128/214 R |
| 4,041,432 A | 8/1977 | Yarworth et al. | 604/89 |
| 4,063,555 A | 12/1977 | Ulinder | 128/214 R |
| 4,094,195 A | 6/1978 | Friswell et al. | 73/422 GC |
| 4,094,196 A | 6/1978 | Friswell | 73/422 GC |
| 4,116,201 A | 9/1978 | Shah | 128/351 |
| 4,121,585 A | 10/1978 | Becker, Jr. | 128/214 R |
| 4,143,853 A | 3/1979 | Abramson | 251/149 |
| 4,223,808 A | 9/1980 | Williams et al. | 222/88 |

(Continued)

FOREIGN PATENT DOCUMENTS

| | | |
|---|---|---|
| EP | 0 268 480 | 5/1988 |
| GB | 2 079 162 A | 7/1980 |
| WO | WO 83/02559 | 8/1983 |
| WO | WO 93/11828 | 6/1993 |
| WO | WO 96/00107 | 1/1996 |
| WO | WO 97/39791 | 10/1997 |
| WO | WO 98/22178 | 5/1998 |
| WO | WO 98/39594 | 9/1998 |
| WO | WO 00/44433 | 8/2000 |

*Primary Examiner*—Michael J. Hayes
*Assistant Examiner*—Jeremy Thisse
(74) *Attorney, Agent, or Firm*—Bromberg & Sunstein LLP

(57) ABSTRACT

A medical valve for valving fluid includes a housing defining a chamber having an inlet, an outlet, and an interior wall, a compressible member within the chamber, and a fluid channel defined by the interior wall. The fluid channel directs fluid received from the inlet toward the outlet.

42 Claims, 9 Drawing Sheets

U.S. PATENT DOCUMENTS

| | | | |
|---|---|---|---|
| 4,300,571 A | 11/1981 | Waldbillig | 128/673 |
| 4,324,239 A | 4/1982 | Gordon et al. | 128/214 R |
| 4,333,455 A | 6/1982 | Bodicky | 128/214.5 |
| 4,334,551 A | 6/1982 | Pfister | 137/614.03 |
| 4,344,435 A | 8/1982 | Aubin | 128/350 R |
| 4,387,879 A | 6/1983 | Tauschinski | 251/149.1 |
| 4,421,296 A | 12/1983 | Stephens | 251/149.7 |
| 4,458,480 A | 7/1984 | Irwin | 60/39.63 |
| 4,496,348 A | 1/1985 | Genese et al. | 604/249 |
| 4,498,658 A | 2/1985 | Mikiya | 251/149.6 |
| 4,534,758 A | 8/1985 | Akers et al. | 604/85 |
| 4,535,820 A | 8/1985 | Raines | 137/854 |
| 4,550,785 A | 11/1985 | Hibbard et al. | 173/134 |
| 4,551,136 A | 11/1985 | Mandl | 604/141 |
| 4,585,435 A | 4/1986 | Vaillancourt | 604/27 |
| 4,596,557 A | 6/1986 | Pexa | 604/86 |
| 4,611,973 A | 9/1986 | Birdwell | 417/342 |
| 4,617,015 A | 10/1986 | Foltz | 604/100 |
| 4,661,110 A | 4/1987 | Fortier et al. | 604/256 |
| 4,675,003 A | 6/1987 | Hooven | 604/9 |
| 4,681,132 A | 7/1987 | Lardner | 137/271 |
| 4,683,905 A | 8/1987 | Vigneau et al. | 137/327.1 |
| 4,683,916 A | 8/1987 | Raines | 137/854 |
| 4,698,061 A | 10/1987 | Makaryk et al. | 604/408 |
| 4,710,168 A | 12/1987 | Schwab et al. | 604/99 |
| 4,712,583 A | 12/1987 | Pelmulder et al. | 137/852 |
| 4,743,235 A | 5/1988 | Waldbillig et al. | 604/250 |
| 4,745,950 A | 5/1988 | Mathieu | 137/798 |
| 4,749,003 A | 6/1988 | Lesson | 137/84 |
| 4,752,287 A | 6/1988 | Kurtz et al. | 604/993 |
| 4,752,292 A | 6/1988 | Lopez et al. | 604/244 |
| 4,758,224 A | 7/1988 | Siposs | 604/119 |
| 4,776,369 A | 10/1988 | Lardner et al. | 137/515.5 |
| 4,809,679 A | 3/1989 | Shimonaka et al. | 128/4 |
| 4,816,020 A | 3/1989 | Brownell | 604/97 |
| 4,819,684 A | 4/1989 | Zaugg et al. | 137/112 |
| 4,850,978 A | 7/1989 | Dudar et al. | 604/201 |
| 4,874,377 A | 10/1989 | Newgard et al. | 604/167 |
| 4,915,687 A | 4/1990 | Sivert | 604/83 |
| 4,917,668 A | 4/1990 | Haindl | 604/167 |
| 4,935,010 A | 6/1990 | Cox et al. | 604/122 |
| 4,966,199 A | 10/1990 | Ruschke | 137/843 |
| 5,006,114 A | 4/1991 | Rogers et al. | 604/167 |
| 5,041,087 A | 8/1991 | Loo et al. | 604/83 |
| 5,048,537 A | 9/1991 | Messinger | 128/673 |
| 5,049,128 A | 9/1991 | Duquette | 604/83 |
| 5,059,175 A | 10/1991 | Hanover et al. | 604/891.1 |
| 5,080,654 A | 1/1992 | Pichs et al. | 604/167 |
| 5,085,645 A | 2/1992 | Purdy et al. | 604/167 |
| 5,100,394 A | 3/1992 | Dudar et al. | 604/283 |
| 5,108,380 A | 4/1992 | Herlitze et al. | 604/283 |
| 5,147,333 A | 9/1992 | Raines | 604/249 |
| 5,171,230 A | 12/1992 | Eland et al. | 604/250 |
| 5,171,239 A | 12/1992 | Eland et al. | 604/250 |
| 5,199,947 A | 4/1993 | Lopez et al. | 604/56 |
| 5,201,715 A | 4/1993 | Masters | 604/175 |
| 5,203,775 A | 4/1993 | Frank et al. | 604/256 |
| 5,215,538 A | 6/1993 | Larkin | 604/249 |
| 5,221,271 A | 6/1993 | Nicholson et al. | 604/283 |
| 5,230,706 A | 7/1993 | Duquette | 604/83 |
| 5,242,393 A | 9/1993 | Brimhall et al. | 604/86 |
| 5,242,432 A | 9/1993 | DeFrank | 604/284 |
| 5,269,771 A | 12/1993 | Thomas et al. | 604/213 |
| 5,280,876 A | 1/1994 | Atkins | 251/149 |
| 5,300,034 A | 4/1994 | Behnke et al. | 604/167 |
| 5,320,328 A | 6/1994 | Decloux et al. | 251/326 |
| 5,330,435 A | 7/1994 | Vaillancourt | 604/167 |
| 5,349,984 A | 9/1994 | Weinheimer et al. | 137/543.21 |
| 5,360,413 A | 11/1994 | Leason et al. | 604/249 |
| 5,380,306 A | 1/1995 | Binon | 604/244 |
| 5,390,898 A | 2/1995 | Smedley et al. | 251/149 |
| 5,401,255 A | 3/1995 | Sutherland et al. | 604/247 |
| 5,439,451 A | 8/1995 | Collinson et al. | 604/247 |
| 5,458,640 A | 10/1995 | Gerrone | 604/264 |
| 5,465,938 A | 11/1995 | Werge et al. | 251/149.1 |
| 5,474,536 A | 12/1995 | Bonaldo | 604/86 |
| 5,474,544 A | 12/1995 | Lynn | 604/283 |
| 5,509,433 A | 4/1996 | Paradis | 137/1 |
| 5,509,912 A | 4/1996 | Vaillancourt et al. | 604/283 |
| 5,520,666 A | 5/1996 | Choudhury et al. | 604/283 |
| 5,533,708 A | 7/1996 | Atkinson et al. | 251/149.1 |
| 5,533,983 A | 7/1996 | Haining | 604/249 |
| 5,549,566 A | 8/1996 | Elias et al. | 604/167 |
| 5,569,209 A | 10/1996 | Roitman | 604/190 |
| 5,569,235 A | 10/1996 | Ross et al. | 604/403 |
| 5,573,516 A | 11/1996 | Tyner | 604/249 |
| 5,578,059 A | 11/1996 | Patzer | 604/249 |
| 5,616,129 A | 4/1997 | Mayer | 604/167 |
| 5,616,130 A | 4/1997 | Mayer | 604/167 |
| 5,620,434 A | 4/1997 | Brony | 604/406 |
| 5,674,206 A | 10/1997 | Alton et al. | 604/249 |
| 5,676,346 A | 10/1997 | Leinsing | 251/149.1 |
| 5,685,866 A | 11/1997 | Lopez | 604/249 |
| 5,694,686 A | 12/1997 | Lopez | 29/890.126 |
| 5,695,466 A | 12/1997 | Lopez et al. | 604/93 |
| 5,699,821 A | 12/1997 | Paradis | 137/1 |
| 5,700,248 A | 12/1997 | Lopez | 604/249 |
| 5,749,861 A | 5/1998 | Guala et al. | 604/249 |
| RE35,841 E | 7/1998 | Frank et al. | 604/256 |
| 5,806,831 A | 9/1998 | Paradis | 521/149.1 |
| 5,820,601 A | 10/1998 | Mayer | 604/167 |
| 5,921,264 A | 7/1999 | Paradis | 137/15 |
| 6,029,946 A | 2/2000 | Doyle | 251/149.1 |
| 6,036,171 A | 3/2000 | Weinheimer et al. | 251/149 |
| 6,039,302 A | 3/2000 | Cote, Sr. et al. | 251/149 |
| 6,050,978 A | 4/2000 | Orr et al. | 604/249 |
| 6,068,011 A | 5/2000 | Paradis | 137/1 |
| 6,089,541 A | 7/2000 | Weinheimer et al. | 251/149 |
| 6,152,900 A | 11/2000 | Mayer | 604/167 |
| 6,245,048 B1 | 6/2001 | Fangrow, Jr. et al. | 604/249 |
| 6,290,206 B1 | 9/2001 | Doyle | 251/149.1 |

APPARATUS FOR REDUCING FLUID DRAWBACK THROUGH A MEDICAL VALVE

This application is a continuation-in-part U.S. patent application Ser. No. 09/394,169, filed Sep. 13, 1999 now U.S. Pat. No. 6,039,302 which is a continuation of U.S. patent application Ser. No. 08/970,125, filed Nov. 13, 1997 now abandoned, which claims priority from U.S. provisional patent application No. 60/034,708, filed Jan. 3, 1997, and U.S. provisional patent application No. 60/031,175, filed Nov. 18, 1996, and also claims priority from U.S. provisional patent application Ser. No. 60/117,359, filed Jan. 27, 1999, and entitled, "Apparatus for Reducing Fluid Drawback Through a Medical Valve."

FIELD OF THE INVENTION

The invention generally relates to medical products and, more particularly, the invention relates to devices for reducing backflow through a medical valve.

BACKGROUND OF THE INVENTION

Medical valving devices commonly are utilized to valve fluids injected into and withdrawn from a patient. One exemplary type of medical valving device, known in the art as a "catheter introducer," maintains a sealed port for accessing the patient's vasculature. Use of such a valve enables vascular access without requiring the patient's skin to be repeatedly pierced by a needle. Moreover, catheter introducers are constructed to withstand a range of back-pressures produced by a patient's blood pressure, thus minimizing blood loss resulting from fluid injections or withdrawals.

Fluid commonly is transferred to/from a patient by inserting a syringe (e.g., a needle) into a medical valve, thus communicating with the patient's vasculature. Problems arise, however, when the syringe is withdrawn from the valve. More particularly, a back pressure produced by withdrawing the syringe undesirably can cause blood to leak proximally into various parts of the valve. In addition to coagulating and impeding the mechanical operation of the valve, blood in the valve also compromises the sterility of the valve.

SUMMARY OF THE INVENTION

In accordance with one aspect of the invention, a medical valve for valving fluid includes a housing defining a chamber having an inlet, an outlet, and an interior wall, a compressible member within the chamber, and a fluid channel defined by the interior wall. The fluid channel directs fluid received from the inlet toward the outlet.

In preferred embodiments, the compressible member does not occlude fluid flow through the fluid channel. The compressible member may be any compressible object that is made from any compressible material known in the art. For example, the compressible member may be made from a sponge material. The compressible member also may be made from a material that merely expands and contracts in response to a mechanical force. For example, the compressible member may be a balloon device. The medical valve also may include a plunder, having a distal end within the interior, that controls the volume of the variable volume interior.

In some embodiments, the valve is movable between open and closed positions. In such case, the compressible member may cooperate with the interior to cause the interior to have a greater available volume (for containing fluid) when the valve is open than when the valve is closed. Accordingly, as the valve closes (and the available volume decreases), residual fluid within the valve should be forced from the chamber toward the outlet of the valve.

In accord with another aspect of the invention, a medical valve having an open mode for permitting fluid flow through the valve, and a closed mode for preventing fluid flow through the valve, includes an interior wall defining a variable volume fluid chamber, and a compressible member within the variable volume fluid chamber. The compressible member and interior wall together define both a closed chamber volume within the fluid chamber when the valve is in the closed mode, and an open chamber volume when the valve is in the open mode. The closed chamber volume preferably is no greater than the open chamber volume, thus reducing the potential for fluid drawback that may result when transitioning from the open mode to the closed mode.

In preferred embodiments, the interior wall defines a channel for channeling fluid flow through the valve. The compressible member preferably does not occlude fluid flow through the valve since it does not occlude the channel.

In accord with other aspects of the invention, a medical valve for valving fluid permits fluid flow when in an open mode and prevents fluid flow when in a closed mode. The valve includes an interior wall defining a chamber, and a compressible member within the chamber. The compressible member has a maximum volume and a minimum volume. The compressible member has a volume that is equal to the maximum volume when the valve is in the closed mode. In a similar manner, the compressible member has a volume that is equal to the minimum volume when in the open mode.

In preferred embodiments, the minimum volume is smaller than the maximum volume. In addition, the interior wall defines a channel for channeling fluid through the valve when in the open mode. In other embodiments, the compressible member and chamber cooperate to define a closed chamber volume when the valve is in the closed mode, and an open chamber volume when the valve is in the open mode. The closed chamber volume preferably is greater than the open chamber volume.

In accordance with yet another aspect of the invention, a medical valve includes a housing defining both a valve chamber and a fluid passageway for directing fluid through the valve, a compressible member within the chamber, and a vent defined by a wall of the chamber (chamber wall) extending through the housing to vent the member chamber. In addition, the valve chamber has an inlet for receiving fluid from the fluid passageway. The compressible member divides the valve chamber into a fluid chamber and a member chamber, where the fluid chamber receives fluid through the inlet and has an outlet for directing fluid to the fluid passageway. The member chamber is defined by the compressible member and the chamber wall and thus, includes the vent.

BRIEF DESCRIPTION OF THE DRAWINGS

The foregoing and other objects and advantages of the invention will be appreciated more fully from the following further description thereof with reference to the accompanying drawings wherein.

DESCRIPTION OF PREFERRED EMBODIMENTS

Figure 1:
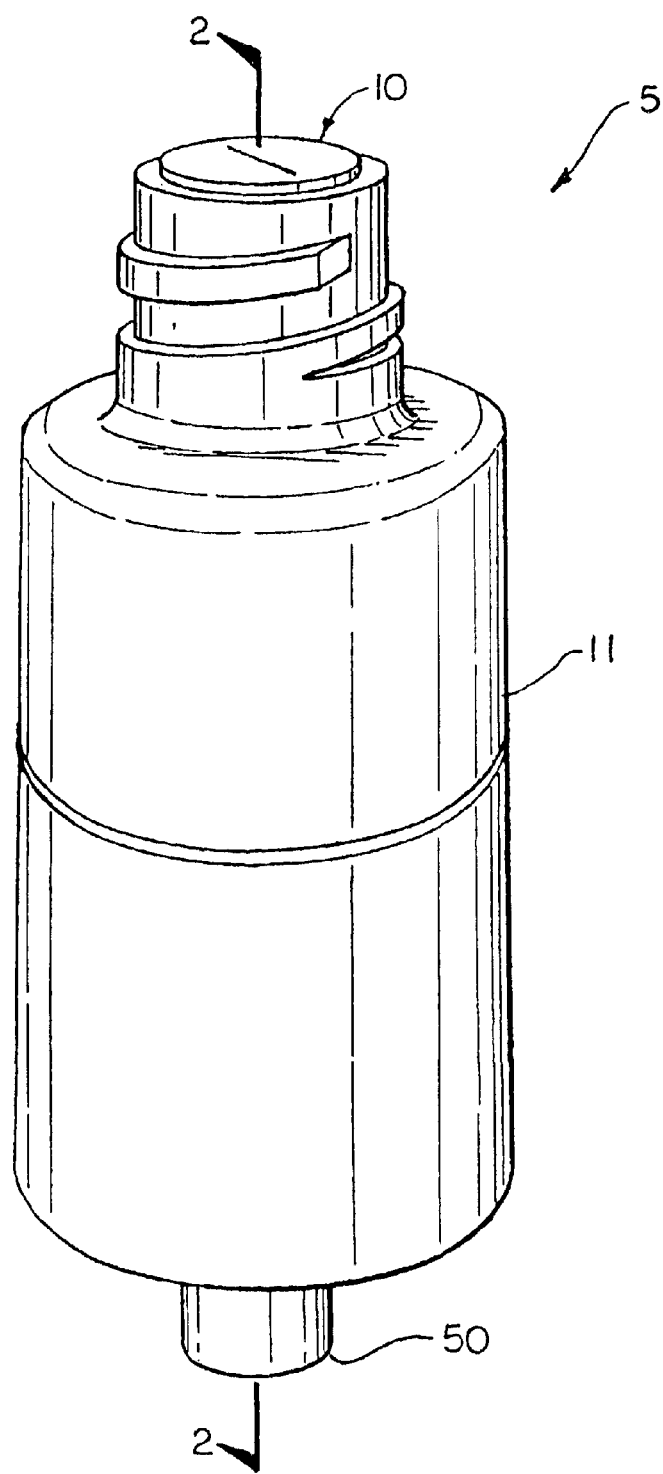
FIG. 1 schematically shows a medical valve that-may be constructed in accord with preferred embodiments of the invention.

FIG. 1 schematically shows a medical valve 5 that preferably is configured to reduce fluid drawback (a/k/a "backflow") when a syringe or other type of nozzle is withdrawn from it. Accordingly, the valve 5 includes a proximal fluid port 10 for receiving the nozzle, a valve body 11 having a valving mechanism (FIGS. 2 and 3A–3D) that controls fluid flow through the valve 5, and a distally located fluid port 50 for directing fluid between the valve 5 and a patient. The fluid preferably is in liquid form, such as liquid medication. Although much of the discussion herein refers to the proximal port 10 as a fluid inlet, and the distal port 50 as a fluid outlet, the proximal and distal ports 10 and 50 also may be utilized respectively as outlet and inlet ports. In preferred embodiments, the valve 5 is similar to that disclosed in co-pending U.S. patent application Ser. No. 09/394,169, entitled, "SWABBABLE LUER-ACTIVATED VALVE," filed Sep. 13, 1999 and naming Andrew Cote and Charles Ganem as inventors, the disclosure of which is incorporated herein, in its entirety, by reference. It should be noted that although preferred embodiments are discussed with reference to the above noted patent application, principles of the invention may be applied to other medical valve devices having dissimilar structures to those medical valves shown. As discussed below, the distal port 50 of the valve 5 may be at its location shown in FIG. 1, or at a location that is orthogonal to the longitudinal dimension of the valve 5.

Figure 2:
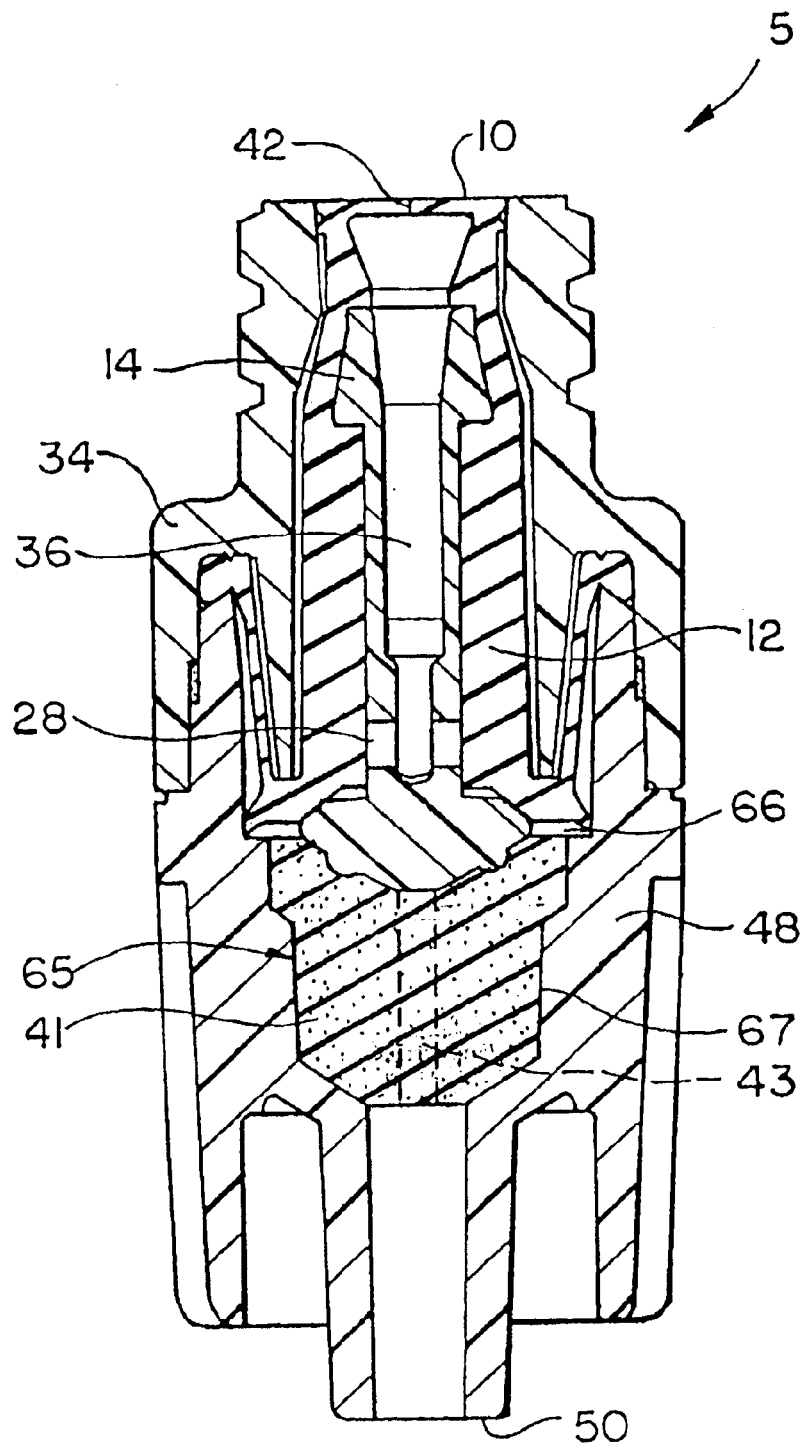
FIG. 2 schematically shows a cross-sectional view of a first illustrative embodiment of the medical valve shown in FIG. 1 along line 2—2.

FIG. 2 schematically shows a cross-sectional view of a first embodiment of the medical valve 5 shown in FIG. 1 along line 2—2. Among other things, the valve 5 includes an inlet housing portion 34 having the proximal port 10, an outlet housing portion 48 having the distal port 50, a stretchable and compressible gland 12 secured between the inlet housing 34 and outlet housing 48, and a rigid, longitudinally movable cannula 14 secured within the valve 5 by the gland 12. The cannula 14 forms a cannula flow channel 36 terminating at a transverse channel 28 that normally is occluded by the gland 12. In addition, the outlet housing 48 forms a chamber 65 having a volume that changes as the cannula 14 is urged proximally and distally by a nozzle.

Insertion of a nozzle against a slit 42 at the proximal end of the gland 12 causes the cannula 14 to move distally, thereby moving the transverse channel 28 from its occluding contact with the gland 12. Liquid then may be directed first through the cannula channel 36 and transverse channel 28, then through the variable volume chamber 65, and out of the valve 5 through the distal port 50. Details of the cooperation of the various valving mechanisms within the valve 5 are more fully described in the aforementioned co-pending U.S. patent application.

In accord with preferred embodiments of the invention, the valve 5 also includes a compressible member 41 positioned within the chamber 65, and one or more narrow flow channels formed in the interior wall forming the chamber 65. One exemplary narrow flow channel is shown in phantom at reference number 43. The compressible member 41 cooperates with the cannula 14 to reduce the available volume within the chamber 65 that may be utilized to contain fluid within the valve 5. In preferred embodiments, the compressible member 41 occupies substantially the entire volume of the chamber 65 when the valve 5 is closed (i.e., in a "closed mode").

The narrow flow channels 43 are not occluded by the compressible member 41 and thus, are utilized to direct fluid around the compressible member 41 and toward the distal port 50. In preferred embodiments, the narrow flow channels 43 are in the form of relatively deep and narrow grooves formed in the interior walls of the distal housing 48. It is anticipated that flow channels 43 having a depth of about 0.040–0.060 inches, and a width of about 0.020–0.040 inches would produce satisfactory results. These dimensions are not exact, however, and may be modified as necessary. Accordingly, practice of the invention should not be limited to these preferred dimensions. In preferred embodiments, the valve 5 includes three independent grooves longitudinally spaced about 120 degrees apart across the cylindrical inner surface of the variable volume chamber 65.

The compressible member 41 may be any apparatus that performs the dual function of compressing and expanding within the chamber 65, and limiting available chamber volume for containing liquid. Accordingly, such a member 41 directs liquid to the narrow channels 43, thus bypassing the chamber 65. In preferred embodiments, the compressible member 41 is a medical grade closed cell sponge rubber that is produced by conventional injection molding processes. Such member 41 may be made by injecting an elastomeric material with a nitrogen gas, and surrounding the injected elastomer with an outside skin, such as rubber. As shown in the figures, the compressible member 41 of this embodiment occupies most of the volume of the chamber 65 at all times (i.e., between the times when the valve 5 is opened, and when the valve 5 is closed).

In alternative embodiments, the compressible member 41 is a latex or polyester balloon having a hollow interior. The balloon changes shape based upon the position of the cannula 14. Regardless of the type of apparatus is used as the compressible member 41, however, its use necessarily adds a degree of mechanical resistance to the longitudinal movement of the cannula 14.

Figure 3A:
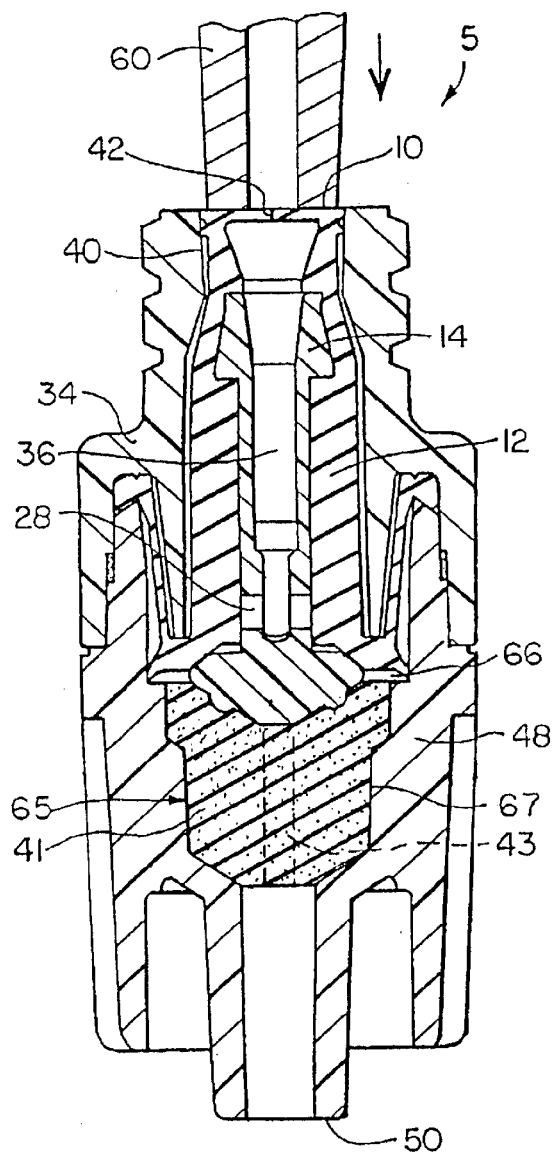
FIGS. 3A–3D schematically show the cross-sectional view of the valve shown in FIG. 2 as it is urged from a closed mode to an open mode.
Figure 3B:
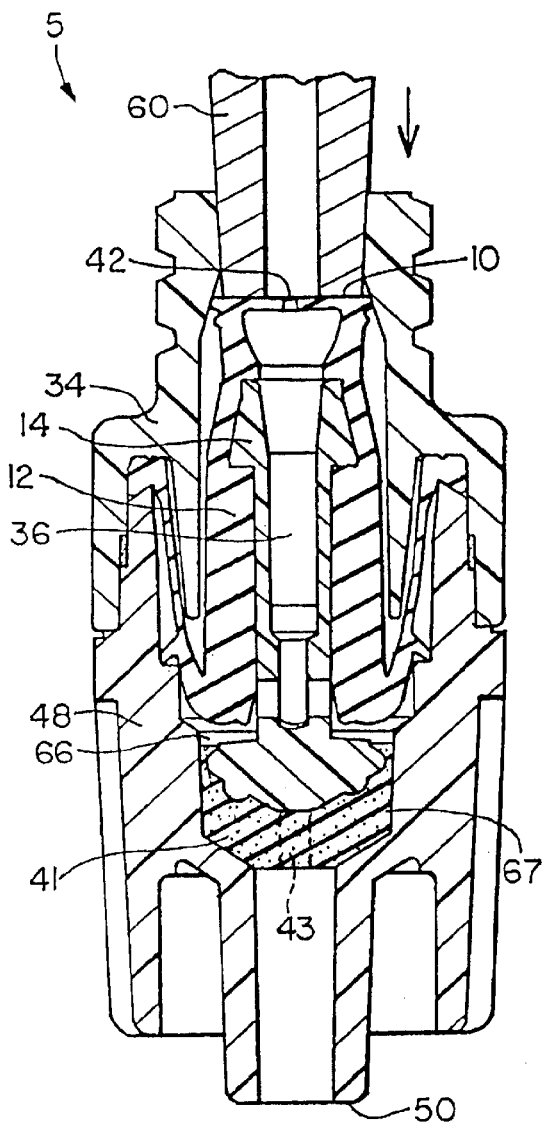
Figure 3C:
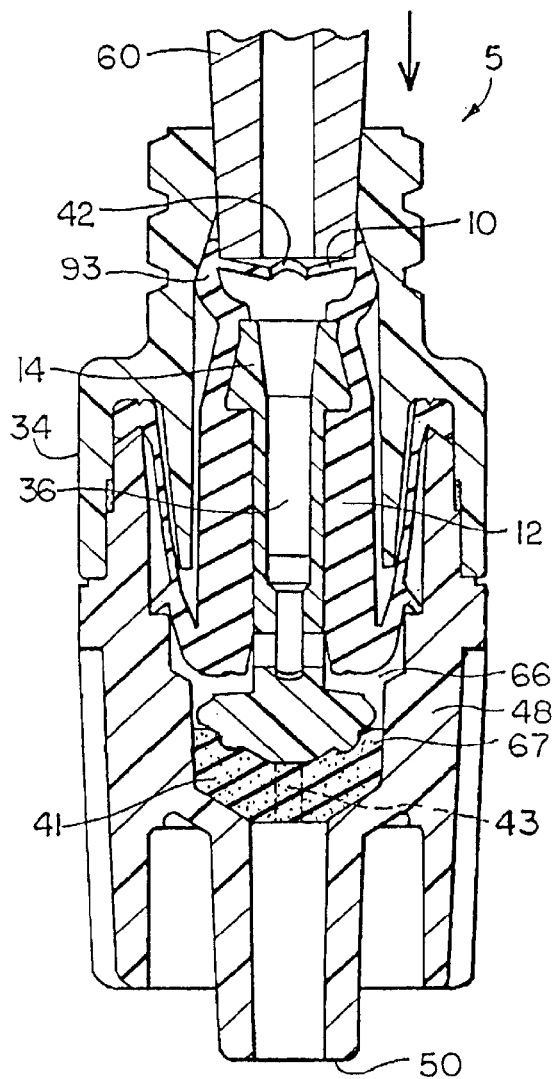
Figure 3D:
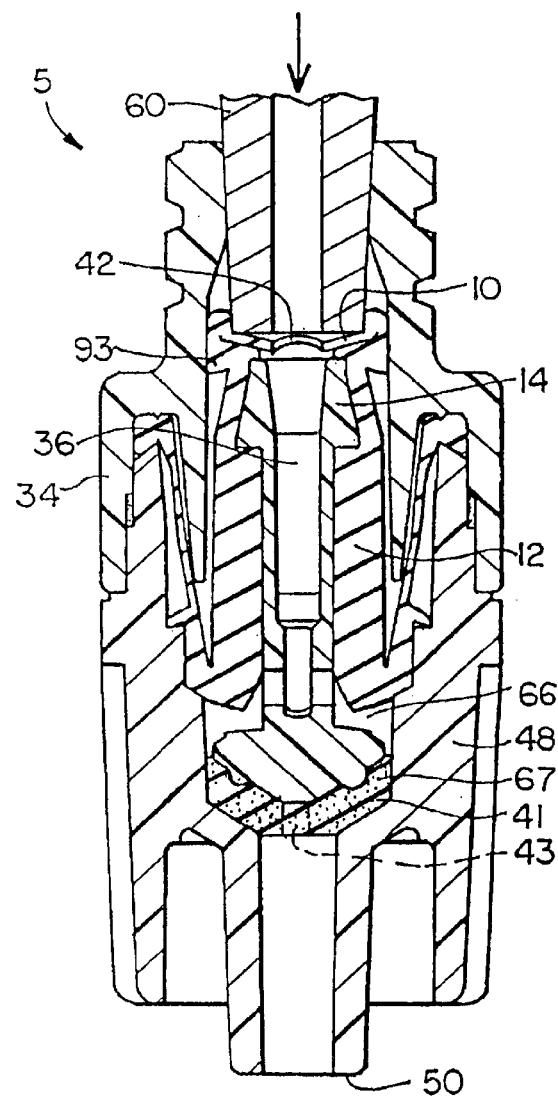

FIGS. 3A–3D schematically show the cross-sectional view of the valve 5 shown in FIG. 2 as it is urged from a closed mode to an open mode. More particularly, FIG. 3A shows the valve 5 as a nozzle is about to be inserted through the proximal port 10. FIGS. 3B–3D show the nozzle at various stages of progression through the proximal port 10 and into the inlet housing 34. More particularly, as shown in FIG. 3A, the compressible member 41 occupies substantially all of the chamber volume when the valve 5 is in the closed mode. As the nozzle is inserted, however, the compressible member 41 compresses between the (distally moving) distal end of the cannula 14 (that acts as a plunger) and the distal end of the interior wall of the chamber 65. As the compressible member 41 compresses (i.e., thereby having a decreasing volume), a proximal region of the chamber 65 (hereinafter "proximal chamber 66") begins to form and increase in size until the valve 5 is in the fully open mode (FIG. 3D). When the valve 5 is in the fully open position, the compressible member 41 is compressed to a minimum volume within a distal portion of the chamber 65 (hereinafter "distal chamber 67"). In some embodiments, the proximal chamber 66 has a volume that is about equal to or less than that of the distal chamber 67.

The total available volume for containing liquid in the chamber 65 preferably is greater when the valve 5 is open than when the valve 5 is closed. Accordingly, when in the open mode (FIG. 3D), liquid can collect in the proximal chamber 66. As the nozzle is withdrawn, the volume of the proximal chamber 66 reduces and the volume of the compressible member 41 increases. This forces liquid from the proximal chamber 66 into the narrow channels 43, and then out the distal port 50. When the valve 5 returns to the closed mode, the proximal chamber 66 has a minimum volume while the compressible member 41 has a maximum volume. As the valve 5 returns to closed mode, liquid formerly in the proximal region in excess of the minimum proximal chamber volume thus was forced from the proximal chamber 66, into the narrow channels 43, and toward the distal port 50. As can be deduced by those skilled in the art, this creates a positive pressure from the distal port 50, consequently preventing (or substantially reducing) fluid drawback that can cause blood or other contaminants to be drawn into the valve 5.

Instead of the narrow channels 43, liquid may be directed to the distal port 50 by some other means. Accordingly, principles of the invention should not be limited to those embodiments requiring narrow channels 43.

Figure 4:
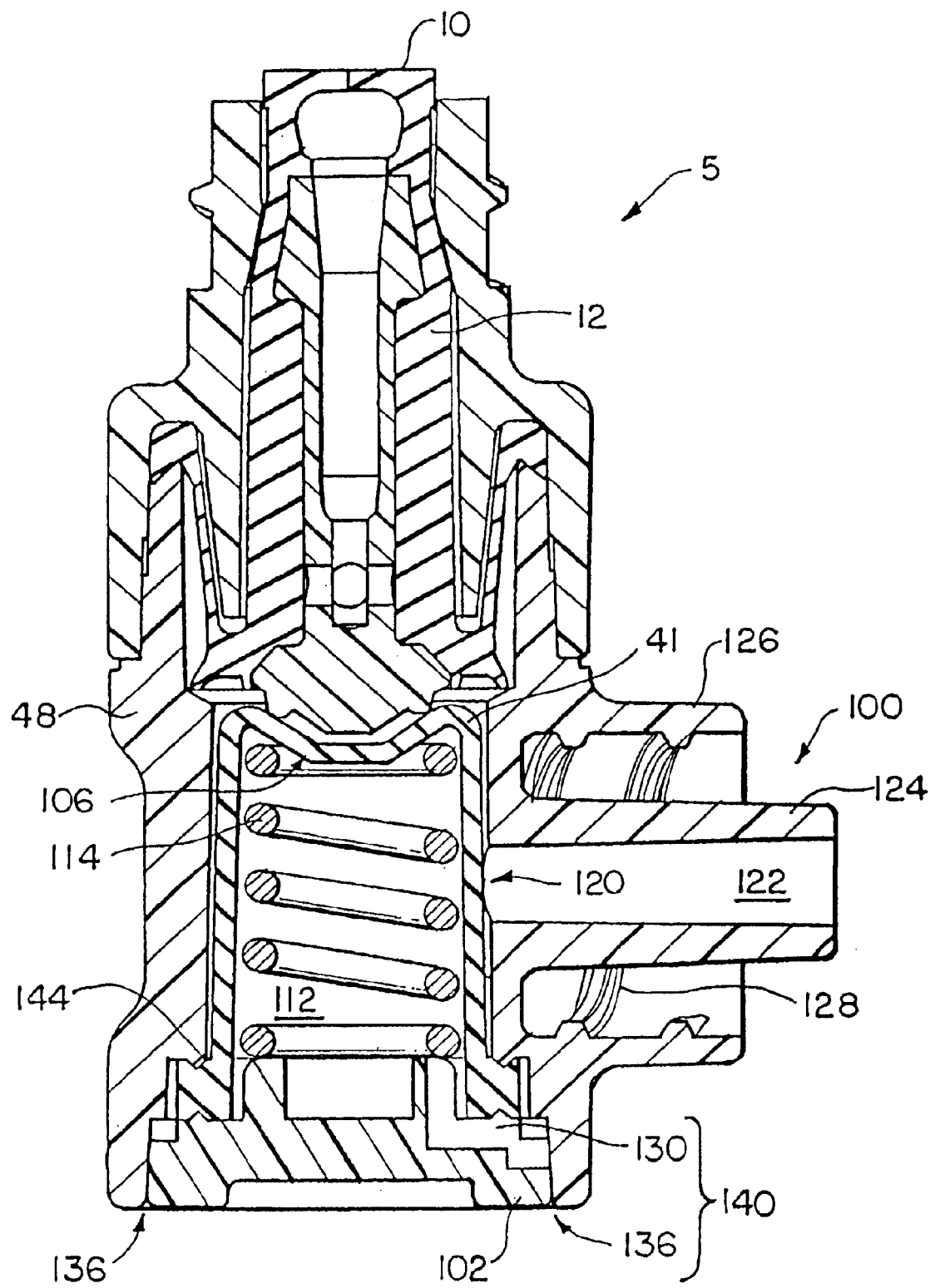
FIG. 4 schematically shows a cross-sectional view of a second illustrative embodiment of the valve shown in FIG. 1.
Figure 5A:
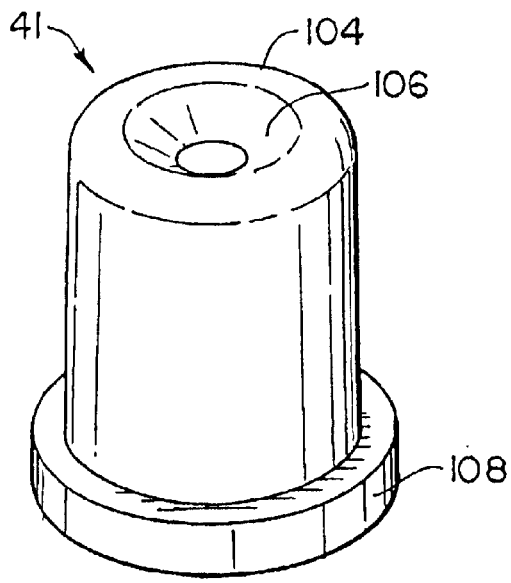
FIG. 5A shows a perspective view of a compressible member utilized with the second illustrative embodiment of the valve.

FIG. 4 shows a cross-sectional view of a second embodiment of the valve 5 shown in FIG. 1. In this embodiment, the outlet housing portion 48 is reconfigured to have an orthogonal outlet 100 for directing fluid from the valve 5, and an end cap 102 at its distal end. Further unlike the embodiment shown in FIG. 1, the compressible member 41 is in the form of a hollow cylinder having a closed top portion, and an open bottom portion (FIG. 5A). In particular, the top portion comprises a top surface 104 having a depression 106 for receiving the bottom portion of the cannula 14. The bottom portion includes an annular flange 108 for securing the compressible member 41 within the valve 5 (discussed below). The compressible member 41 may be manufactured from any material used in the art, such as silicone, latex, or plastic, that can compress and decompress without significantly affecting its overall structure.

As shown in FIG. 4, the compressible member 41 is free standing within the chamber 65. Accordingly, when in the closed mode, the side of the compressible member 41 do not directly contact the side walls of the fluid chamber 65. In illustrative embodiments, the side of the compressible member 41 is between about 0.002–0.010 inches from the side walls of the chamber 65. This distance from the interior walls of the chamber 65 provides some additional clearance for compressing the compressible member 41. In other embodiments, there is no such clearance and thus, the compressible member 41 compresses by collapsing upon its interior only.

Figure 6:
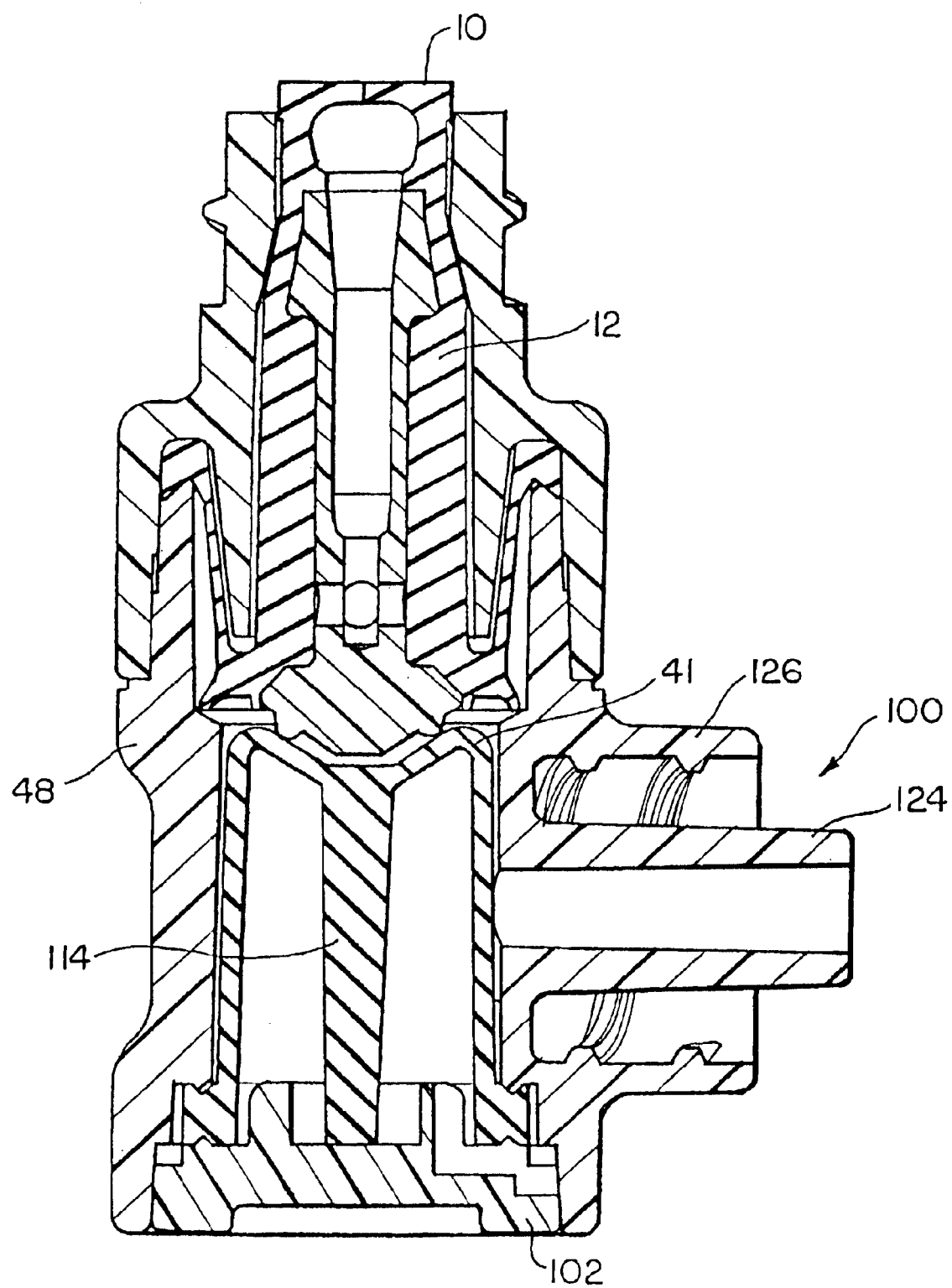
FIG. 6 schematically shows a cross-sectional view of a third illustrative embodiment of the valve shown in FIG. 1.

The compressible member 41 in this embodiment (FIG. 4) includes a member interior 112 having a conventional spring 114 disposed therein. Although not necessary in many embodiments, the spring 114 may be provided to supply additional proximal biasing force for normally biasing the member 41 in a proximal direction. The spring 114 may be any spring known in the art, such as a coil spring, or an integral piece of material that provides the additional biasing force (FIG. 6). In other embodiments, the member interior 112 is empty and thus, it has no internal spring 114. In such other embodiments, the compressible member 41 preferably is manufactured from a material and/or with a geometry that normally biases the compressible member 41 proximally. In fact, such embodiments of the compressible member 41 themselves are springs. Additional details of such member geometry are discussed below with reference to FIG. 7.

As noted above, the valve 5 shown in FIGS. 4 and 6 also differ from that shown in FIG. 1 in that it includes the outlet that extends from the side of the valve 5. In particular, the chamber 65 includes an interior wall that defines an opening 120 to an outlet channel 122 that is formed through an outlet tube 124. The outlet tube 124 may include an annular skirt 126 having threads 128 for coupling with a complimentary connector device. The outlet tube 124 thus is substantially orthogonal to the longitudinal dimension of the valve 5. In some versions of this embodiment, the compressible member 41 may be positioned in the chamber 65 to normally occlude the outlet, thus preventing fluid flow from the chamber 65.

Figure 5B:
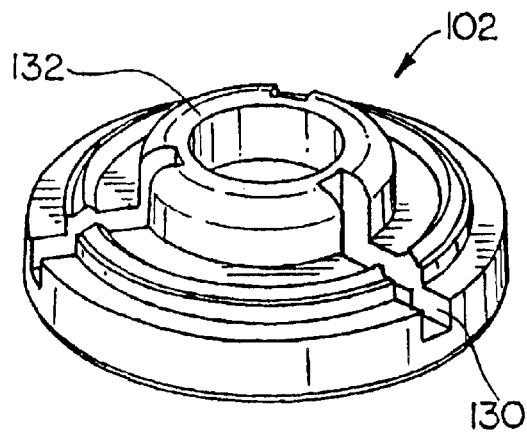
FIG. 5B shows a perspective view of an end cap utilized with various embodiments of the valve.
Figure 5C:
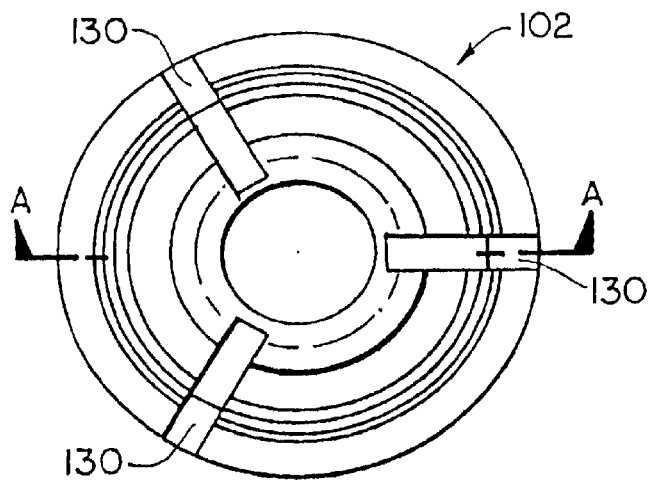
FIG. 5C shows a plan view of the end cap shown in FIG. 5B.
Figure 5D:
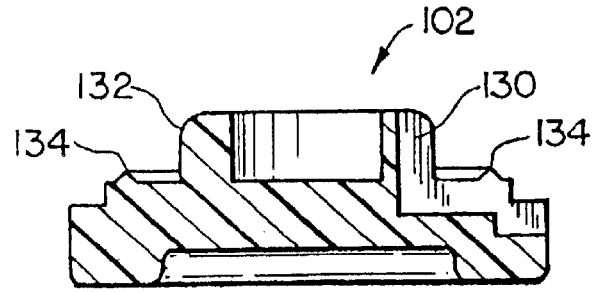
FIG. 5D shows a cross-sectional view of the end cap shown along line A—A of FIG. 5C.

Further unlike the embodiment shown in FIG. 1 (as noted above), the second illustrative embodiment of the valve 5 also includes the end cap 102, which is ultrasonically welded to its proximal end. As shown in FIGS. 5B–5D, the end cap 102 includes a top surface that forms a part of the member interior 112. The top surface thus defines three venting grooves 130, an annular protrusion 132 for securing the spring 114 (if any) within the member interior 112, and an annular ridge 134 for mating with a complimentary part of the valve housing for securing the end cap 102 to the valve 5.

The cap 102 preferably is connected to the distal end of the housing so that it defines a small annular space 136 ("cap space 136," or referred to by those skilled in the art as a "reveal") between it and the housing. In preferred embodiments, the cap space 136 is between about 0.002 and 0.004 inches. The bottom portion of the compressible member 41 is secured over the three venting grooves 130 to the top surface of the cap 102. Each groove is in fluid communication with the cap space 136 to form a vent 140 that vents the member interior 112 to the exterior of the valve 5. Of course, vents may be interpreted herein to include any channel that extends from the member interior 112 to the exterior of the valve 5. Accordingly, various embodiments of the invention are not to be limited to the specific disclosed vent configurations.

The member interior 112 preferably is fluidly isolated from the rest of the chamber 65 (i.e., the chamber area that is exterior to the compressible member 41). To that end, the outlet housing portion 48 includes a distal rim 144 that, when coupled with the end cap 102, compresses the annular flange 108 around the bottom portion of the compressible member 41 to form a liquid tight pinch-fit seal. This seal ensures that liquid does not leak into the member interior 112. Accordingly, the rim 144 may be flat, or may converge to a pointed annular ring that pinches the member annular flange 108.

When the compressible member 41 is compressed, air within the member chamber (i.e., the chamber formed by the interior of the member 41) is forced out of the member interior 112 through the vents, thus facilitating compression of the compressible member 41. Among other ways, the resistence to compressing the compressible member 41 may be adjusted by adjusting the size and geometry of the vents. Conversely, when the compressible member 41 is decompressed, air from the exterior of the valve 5 is drawn into the member interior 112, thus facilitating decompression of the compressible member 41.

Accordingly, when in the closed mode, the compressible member 41 is fully decompressed, thus causing the proximal chamber 66 to have a minimum volume. When in the open mode, the compressible member 41 is compressed to enlarge the proximal chamber 66 to its maximum volume. Liquid or other fluid injected through the cannula 14 and transverse gland 12 28 thus flows into the proximal chamber 66, and out of the valve 5 through the outlet. To direct fluid to the outlet, this embodiment of the valve 5 may have one or more narrow flow channels (similar to those in the valve 5 of FIG. 1), or the clearance between the compressible member 41 and the interior wall of the chamber 65 may form a channel. In yet other versions of this embodiment, the compressible member 41 normally occludes the outlet. Accordingly, to open the valve 5, the compressible member 41 of this version must be forced distally until the top of the compressible member 41 is more distal than the top of the outlet channel 122, thus fluidly 1≡communicating the proximal chamber 66 with the outlet.

Figure 7:
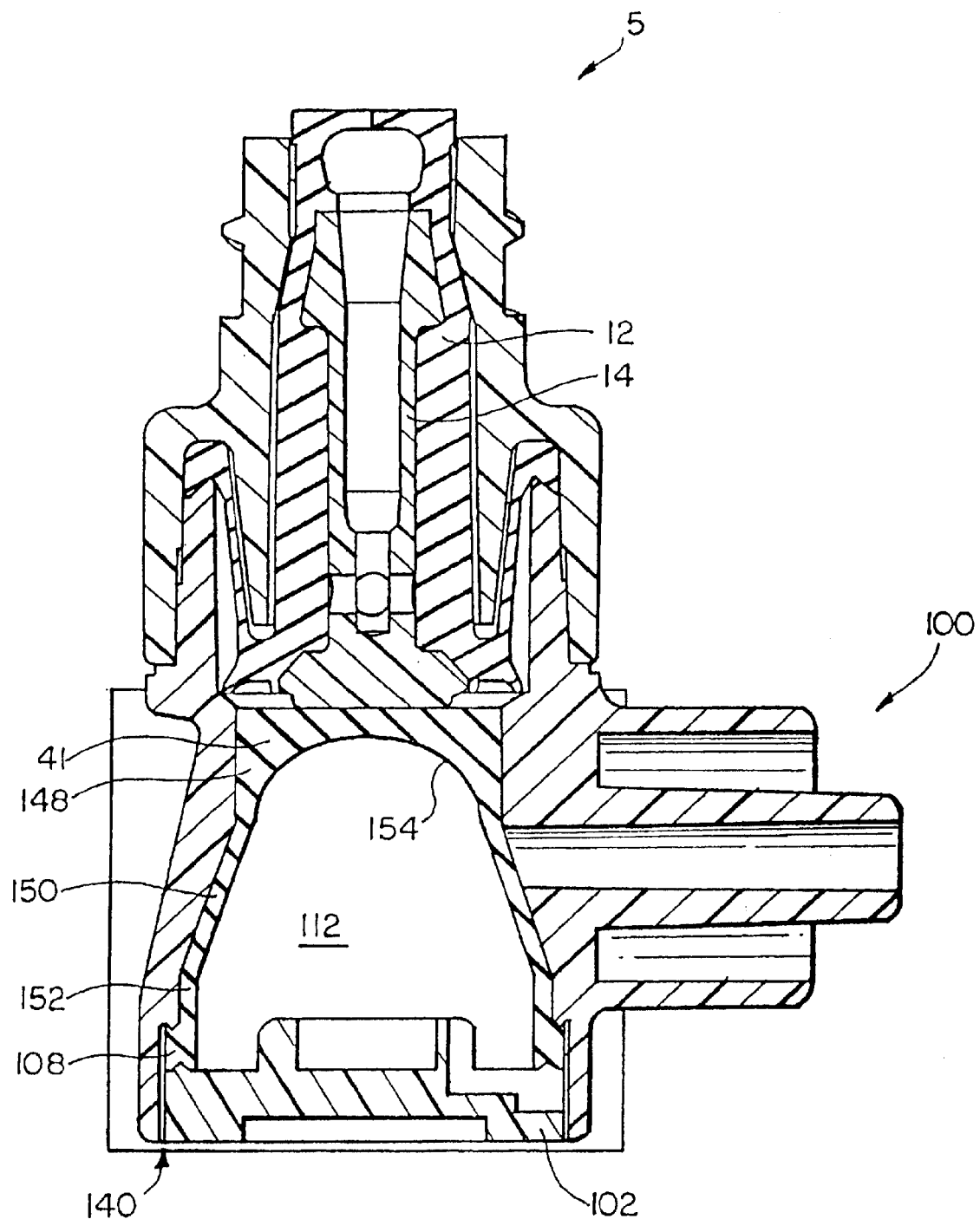
FIG. 7 schematically shows a cross-sectional view of a fourth illustrative embodiment of the valve shown in FIG. 1.

FIG. 7 shows a cross-section of a third illustrative embodiment of the valve 5 shown in FIG. 1. In a manner similar to that shown in FIG. 4, this embodiment includes the orthogonal outlet 100, the compressible member 41 with an open distal end, and the vented end cap 102. Unlike the embodiment shown in FIG. 4, however, the top portion of the compressible member 41 is contoured to a complimentary shape to that of the bottom portion of the cannula 14. For example, as shown in FIG. 7, both the bottom portion of the cannula 14 and the top portion of the cannula 14 are flat. Each of the embodiments described herein may have a similar complimentary geometry.

In addition, the compressible member 41 also is shaped in a distally bowed configuration to further enhance its proximal biasing force. In particular, the compressible member 41 of this embodiment includes an upper portion 148 having a substantially uniform outer diameter, a diverging middle portion 150 having a distally expanding outer diameter, and a lower portion 152 having a substantially uniform inner diameter. In a manner similar to other embodiments, the lower portion 152 includes the annular flange 108 for securing the compressible member 41 within the complimentary recess of the valve 5. The upper portion 148 includes an inner surface 154 (i.e., defining a portion of the member interior 112) having a substantially uniform radius for providing support for the cannula 14 upon its top portion.

As shown in the figure, this embodiment of the valve 5 does not include a spring with the member interior 112. Although not necessary, one may be provided to further proximally bias the compressible member 41. Some versions of this embodiment may utilize an inverted cone type of compressible member 41 (not shown), where the compressible member 41 has an hourglass shape. Similar to the distally bowed compressible member 41, a compressible member 41 in an inverted cone configuration generally readily returns to its normal uncompressed state when distally applied force is not applied to its top portion.

Figure 8:
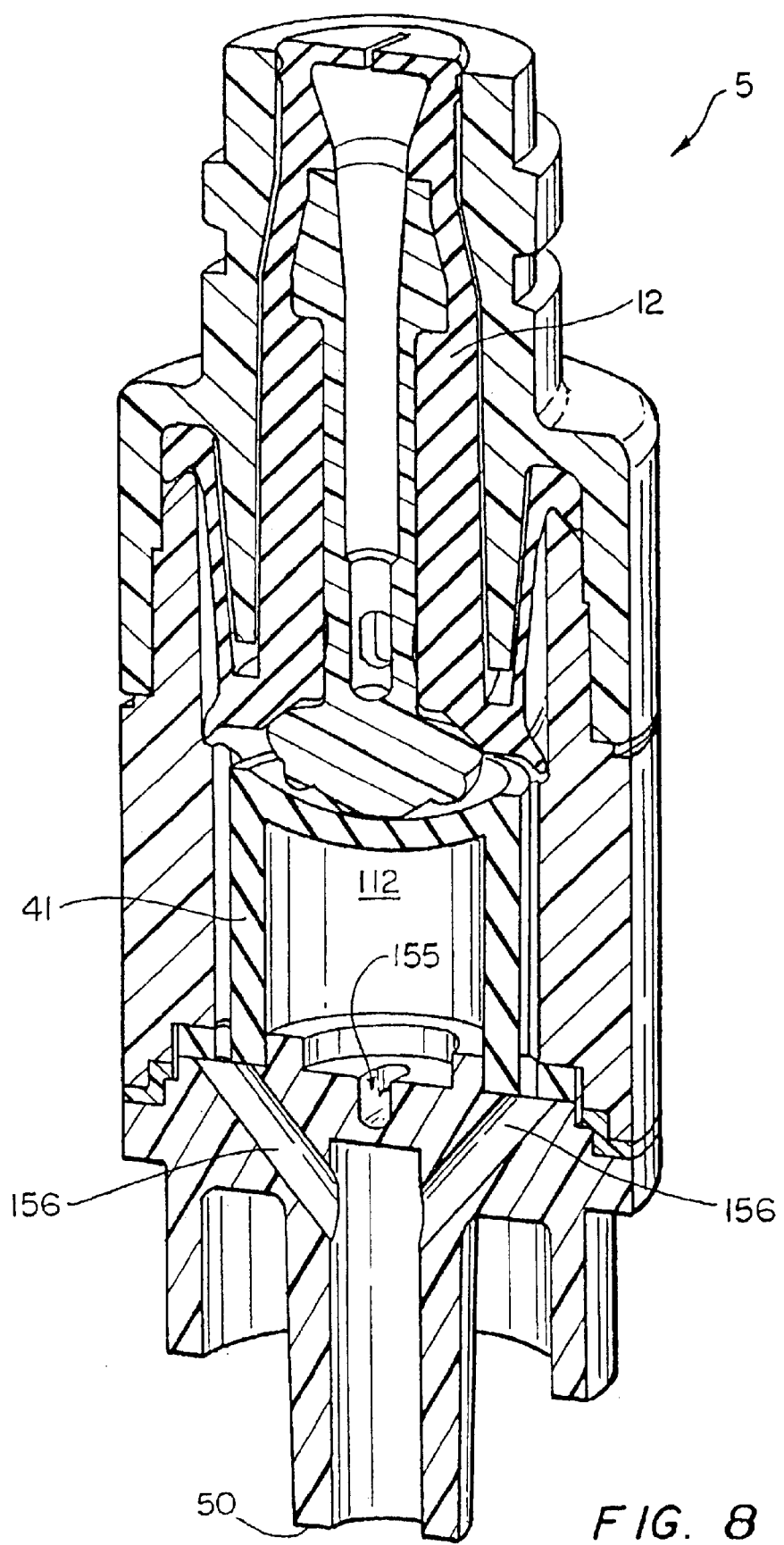
FIG. 8 schematically shows a cross-sectional view of a fifth illustrative embodiment of the valve shown in FIG. 1.

FIG. 8 schematically shows a fourth illustrative embodiment of the valve 5 shown in FIG. 1. In a manner similar to the embodiment shown in FIG. 1, the distal port is located at the proximal end of the valve 5 and not orthogonal to the flow channel through the cannula 14. Also like the embodiment shown in FIGS. 4, 6, and 7, the compressible member 41 is hollow and open distal ended similar to the embodiment shown in FIG. 5A. It should be noted that although the compressible member 41 with a substantially uniform outer diameter is shown, various other compressible members may be utilized, such as the compressible member 41 shown in FIG. 7. Although not shown, some versions of this embodiment include a spring 114 within the member interior 112.

The chamber 65 in the fourth illustrative embodiment forms a vent 155 that extends through the housing, thus venting the member interior 112 to the atmosphere. In addition, this embodiment also includes two distal flow channels 156 that fluidly connect the chamber 65 (i.e., the part of the chamber 65 that is external to the member interior 112) with the distal port 50. Accordingly, when in the open mode, fluid is directed from the proximal chamber 66, through the narrow flow channel(s) 43 in the side of the interior walls to the distal flow channels 156, to the distal port 50. Moreover, when the compressible member 41 is compressed, air is expelled from the member interior 112 via the vent 155. In a similar manner, when the compressible member 41 decompresses, air is drawn into the member interior 112 to facilitate its decompression.

It should be noted that although a swab valve is shown in the disclosed embodiments, other valves may be utilized in accord with the various embodiments disclosed herein. Moreover, in some embodiments implementing a swab valve, the slit top surface of the gland 12 may be substantially flush with the proximal opening to the valve 5 (e.g., see FIG. 8), while in other embodiments, such surface extends above the proximal opening (e.g., see FIG. 4).

Although various exemplary embodiments of the invention have been disclosed, it should be apparent to those skilled in the art that various changes and modifications can be made which will achieve some of the advantages of the invention without departing from the true scope of the invention. These and other obvious modifications are intended to be covered by the appended claims.

We claim:

1. A medical valve for valving fluid, the valve comprising;
   a housing having a fluid passageway therein, the fluid passageway including a chamber;
   a compressible member within the chamber; and
   a movable cannula defining a part of the fluid passageway, the cannula having an inlet with an opening, the opening having a size that is substantially the same size as at least a portion of the part of the fluid passageway through the cannula.

2. The medical valve as defined by claim 1 wherein the cannula controls the volume of the chamber.

3. The medical valve as defined by claim 1 wherein the valve is movable between open and closed positions, the compressible member cooperating with the chamber to cause the interior to have a greater volume when the valve is open than when the valve is closed.

4. The medical valve as defined by claim 1 wherein the chamber has an interior wall defining an air vent.

5. The medical valve as defined by claim 1 wherein the chamber has an internal wall defining a fluid channel, further wherein the compressible member does not occlude fluid flow through the fluid channel.

6. The medical valve as defined by claim 1 wherein the valve is movable between open and closed positions, the compressible member cooperating with the chamber to cause the chamber to have a greater volume for receiving fluid when the valve is open than when the valve is closed.

7. The medical valve as defined by claim 1 wherein the valve permits fluid flow when in an open mode, the valve preventing fluid flow when in a closed mode, the cannula being more distally located when in the open mode than when in the closed mode.

8. The medical valve as defined by claim 1 wherein the compressible member is free standing within the chamber.

9. The medical valve as defined by claim 1 wherein the size of the part of the fluid passageway through the cannula varies.

10. The medical valve as defined by claim 1 wherein the compressible member comprises a sponge material.

11. The medical valve as defined by claim 1 wherein the compressible member comprises a balloon device.

12. A medical valve for valving fluid, the medical valve having an open mode for permitting fluid flow through the valve, the medical valve also having a closed mode for preventing fluid flow through the valve, the medical valve comprising:

a housing having an interior wall defining a variable volume fluid chamber for receiving fluid;

a movable cannula forming at least a part of a fluid passageway through the housing, the cannula having an inlet with an opening, the opening having a size that is substantially the same size as at least a portion of the part of the fluid passageway through the cannula;

a compressible member within the variable volume fluid chamber, the compressible member and interior wall defining a closed chamber volume within the fluid chamber when the valve is in the closed mode, the compressible member and interior wall defining an open chamber volume within the fluid chamber when the valve is in the open mode, the closed chamber volume being less than the open chamber volume.

13. The medical valve as defined by claim 12 wherein the compressible member does not occlude fluid flow through the valve.

14. The medical valve as defined by claim 12 wherein the cannula controls the volume of the chamber.

15. The medical valve as defined by claim 12 wherein the size of the part of the fluid passageway through the cannula varies.

16. The medical valve as defined by claim 12 wherein the compressible member comprises a sponge material.

17. The medical valve as defined by claim 12 wherein the compressible member comprises a balloon device.

18. A medical valve for valving fluid, the valve permitting fluid flow when in an open mode, the valve preventing fluid flow when in a closed mode, the valve comprising;

a housing containing a fluid passageway;

an interior wall defining a chamber, the chamber being within the fluid passageway;

a compressible member within the chamber, the compressible member having a maximum volume and a minimum volume; and a movable cannula having an inner passageway that defines a part of the fluid passageway, the cannula having an inlet with an opening, the opening having a size that is substantially the same size as at least a portion of the part of the fluid passageway through the cannula;

the compressible member having a volume equal to the maximum volume when the valve is in the closed mode;

the compressible member having a volume equal to the minimum volume when the valve is in the open mode.

19. The valve as defined by claim 18 wherein the minimum volume is smaller than the maximum volume.

20. The valve as defined by claim 18 wherein the interior wall defines a channel for channeling fluid through the valve when in the open mode.

21. The valve as defined by claim 18 wherein the compressible member and chamber cooperate to define a dosed chamber volume when the valve is in the closed mode, the compressible member and chamber also defining an open chamber volume when the valve is in the open mode, the closed chamber volume being less than the open chamber volume.

22. The medical valve as defined by claim 18 wherein the size of the part of the fluid passageway through the cannula varies.

23. A medical valve for valving fluid, the medical valve comprising:

a housing containing a fluid passageway for directing fluid through the valve, the housing also containing a valve chamber having an inlet for receiving fluid from the fluid passageway;

movable cannula defining a part of the fluid passageway, the cannula having an inlet with an opening, the opening having a size that is substantially the same size as it least a portion of the part of the fluid passageway through the cannula;

a compressible member within the chamber, the compressible member dividing the valve chamber into a fluid chamber and a member chamber, the fluid chamber receiving fluid from the inlet and having a fluid outlet for directing fluid to the fluid passageway, the member chamber being defined by the compressible member and a chamber wall; and a flexible gland member supporting the cannula within the housing.

24. The medical valve as defined by claim 23 wherein the fluid passageway includes a first passageway portion and a second passageway portion, the first passageway portion being substantially orthogonal to the second passageway portion.

25. The medical valve as defined by claim 23 wherein the member chamber has a volume substantially the same as the volume of the member.

26. The medical valve as defined by claim 23 wherein the member chamber has a volume that is greater than the volume of the fluid chamber.

27. The medical valve as defined by claim 23 wherein the medical valve is alternately usable in an open mode that permits fluid flow through the valve, and a closed mode that prevents fluid flow through the valve.

28. The medical valve as defined by claim 27 wherein the member chamber has a volume that is greater than the volume of the fluid chamber when in the closed mode.

29. The medical valve as defined by claim 27 wherein the member chamber has a volume that is smaller than the volume of the fluid chamber when in the open mode.

30. The medical valve as defined by claim 27 wherein fluid chamber and member chamber each have a variable volume that is dependent upon the mode of the valve.

31. The medical valve as defined by claim 23 wherein the compressible member defines a hollow interior, the compressible member further defining an opening that exposes the hollow interior, the opening being in communication with a vent defined by the member chamber.

32. The medical valve as defined by claim 31 wherein the hollow interior of the compressible member is sealed from fluid communication with the fluid passageway.

33. The medical valve as defined by claim 23 further comprising:
a spring within the compressible member, the spring normally urging the compressible member to an uncompressed state.

34. The medical valve as defined by claim 23 wherein the compressible member is configured to be a spring.

35. The medical valve as defined by claim 23 wherein the compressible member is in a distally bowed configuration that is normally in an uncompressed state.

36. A medical valve for valving fluid, the medical valve comprising:
a housing containing a fluid passageway for directing fluid through the valve, the fluid passageway being formed at least in part by a movable channel means for channeling fluid, the movable channel means having an inlet with an opening, the opening having a size that is substantially the same size as at least a portion of the part of the fluid passageway through the movable channel means;
a valve chamber defined by the housing and being in communication with the fluid passageway; and
means for reducing the volume of the valve chamber.

37. The valve as defined by claim 34 wherein the reducing means comprises a compressible member.

38. The valve as defined by claim 36 further comprising:
means for opening the valve chamber for permitting fluid flow through the valve, the opening means compressing the reducing means as the valve chamber is opened.

39. The medical valve as defined by claim 36 wherein the movable channel means includes a rigid tube.

40. The medical valve as defined by claim 39 wherein the movable channel means includes a cannula.

41. The medical valve as defined by claim 36 further comprising means for venting the reducing means.

42. The medical valve as defined by claim 36 wherein the size of the reducing means expands and contracts based upon the state of the valve.

* * * * *

UNITED STATES PATENT AND TRADEMARK OFFICE
CERTIFICATE OF CORRECTION

PATENT NO. : 6,883,778 B1
DATED : April 26, 2005
INVENTOR(S) : Brian L. Newton et al.

It is certified that error appears in the above-identified patent and that said Letters Patent is hereby corrected as shown below:

Column 8,
Line 44, replace "comprising ;" with -- comprising : --

Column 9,
Line 54, replace "comprising ;" with -- comprising : --

Column 10,
Line 12, replace "dosed" with -- closed --
Line 30, replace "it" with -- at --

Signed and Sealed this

Second Day of August, 2005

JON W. DUDAS
*Director of the United States Patent and Trademark Office*

UNITED STATES PATENT AND TRADEMARK OFFICE
CERTIFICATE OF CORRECTION

PATENT NO. : 6,883,778 B1
DATED : April 26, 2005
INVENTOR(S) : Newton et al.

It is certified that error appears in the above-identified patent and that said Letters Patent is hereby corrected as shown below:

Title page,
Item [63], Related U.S. Application Data, replace "Continuation-in-part" with -- Continuation --.

Column 1,
Line 4, replace "continuation-in-part" with -- continuation of --.

Signed and Sealed this

Fourteenth Day of February, 2006

JON W. DUDAS
*Director of the United States Patent and Trademark Office*